United States Patent [19]

Chee

[11] Patent Number: 5,086,762
[45] Date of Patent: Feb. 11, 1992

[54] TYPING BRACE

[76] Inventor: Edward K. Chee, 220 Bush St., Ste. 348, San Francisco, Calif. 94104

[21] Appl. No.: 669,970

[22] Filed: Mar. 15, 1991

[51] Int. Cl.⁵ .............................. A61F 5/40; A61F 5/37
[52] U.S. Cl. ........................................ 602/4; 128/875; 128/876; 400/715
[58] Field of Search ............. 128/874, 875, 94, 87 R, 128/77, 78, 878; 272/70, 93, 143, DIG. 5, DIG. 9; 2/45, 115; 224/257, 259, 260–262, 266

[56] References Cited

U.S. PATENT DOCUMENTS

| 9,828 | 7/1853 | Day | 128/94 |
|---|---|---|---|
| 982,376 | 1/1911 | Macfarlane | 128/94 |
| 1,745,446 | 2/1930 | Payne | 128/94 |
| 2,796,862 | 6/1957 | Borntraeger | 128/94 |
| 3,108,589 | 10/1963 | Staggs | 128/94 |
| 4,327,909 | 5/1982 | Neufeld | 128/94 |
| 4,337,938 | 7/1982 | Rodriquez | 128/94 |
| 4,601,285 | 7/1986 | Whitchurch | 128/94 |
| 4,751,923 | 6/1988 | Marino | 128/94 |
| 4,815,639 | 3/1989 | Lehman | 128/94 |

Primary Examiner—Robert A. Hafer
Assistant Examiner—Michael Brown
Attorney, Agent, or Firm—Douglas E. White

[57] ABSTRACT

Typing brace apparatus includes a rigid yoke having an upper pair of yoke arms, each yoke arm having a forward end; a leg of the yoke depending downwardly from an intersection of the yoke arms; padding affixed to an inner surface of the yoke; and a pair of straps depending downwardly from the forward end of each yoke arm. A first step of each of the two strap pairs is an elbow strap having an elbow cup at a distal end of the elbow strap and a second strap is a wrist strap having a first human wrist engaging-loop at a distal end of the wrist strap. Buckle for adjusting the length of the straps are included. In one preferred embodiment a waist band for encircling a human waist is operably connected to the yoke leg for stabilizing the yoke leg with respect to the two pairs of straps and the trunk or waist of the typist's body. In a second preferred embodiment, a bracket for attaching the yoke leg to a chair is connected to the yoke leg, again for stabilizing the yoke leg with respect to the two pairs of straps.

19 Claims, 4 Drawing Sheets

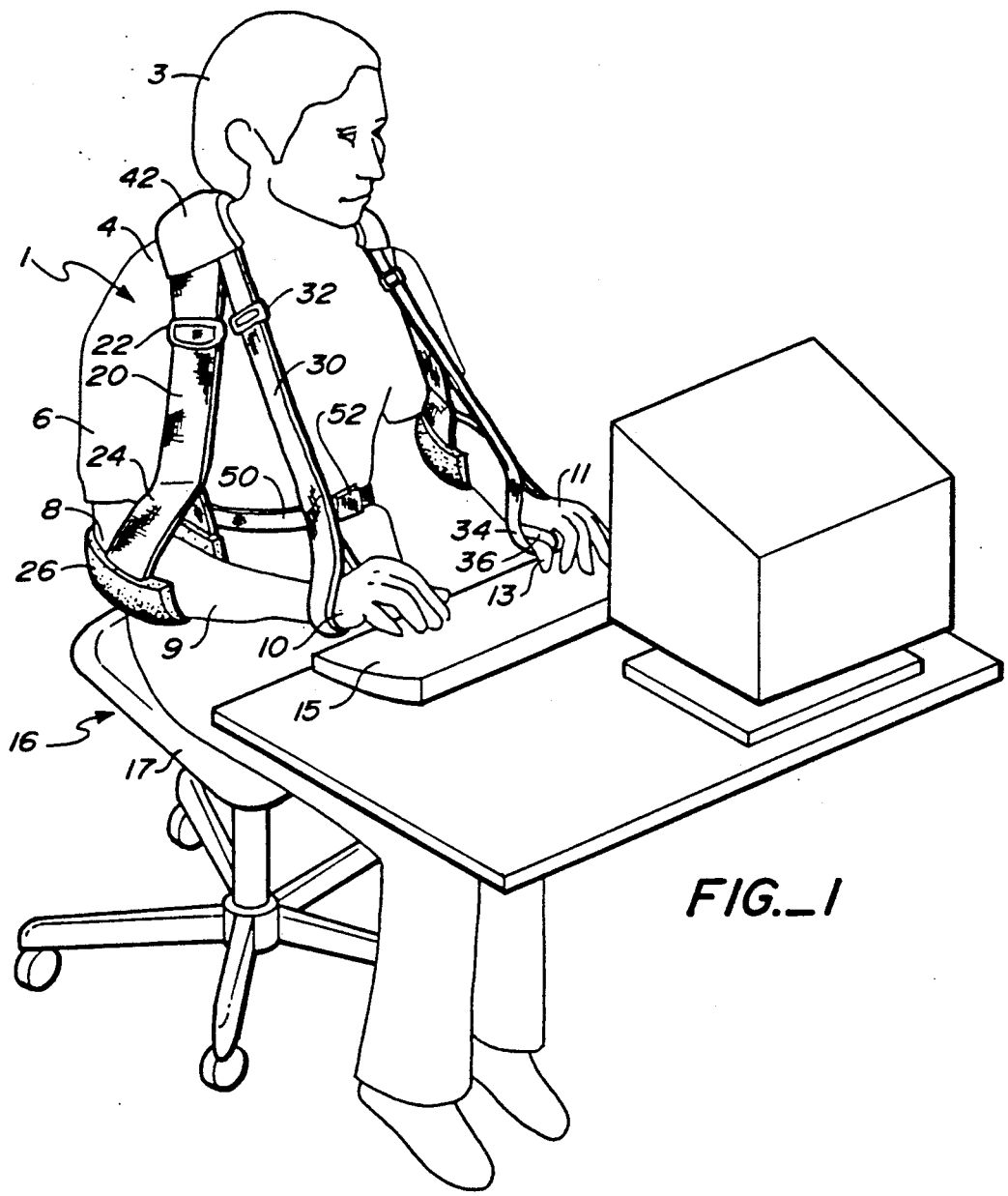
FIG._1

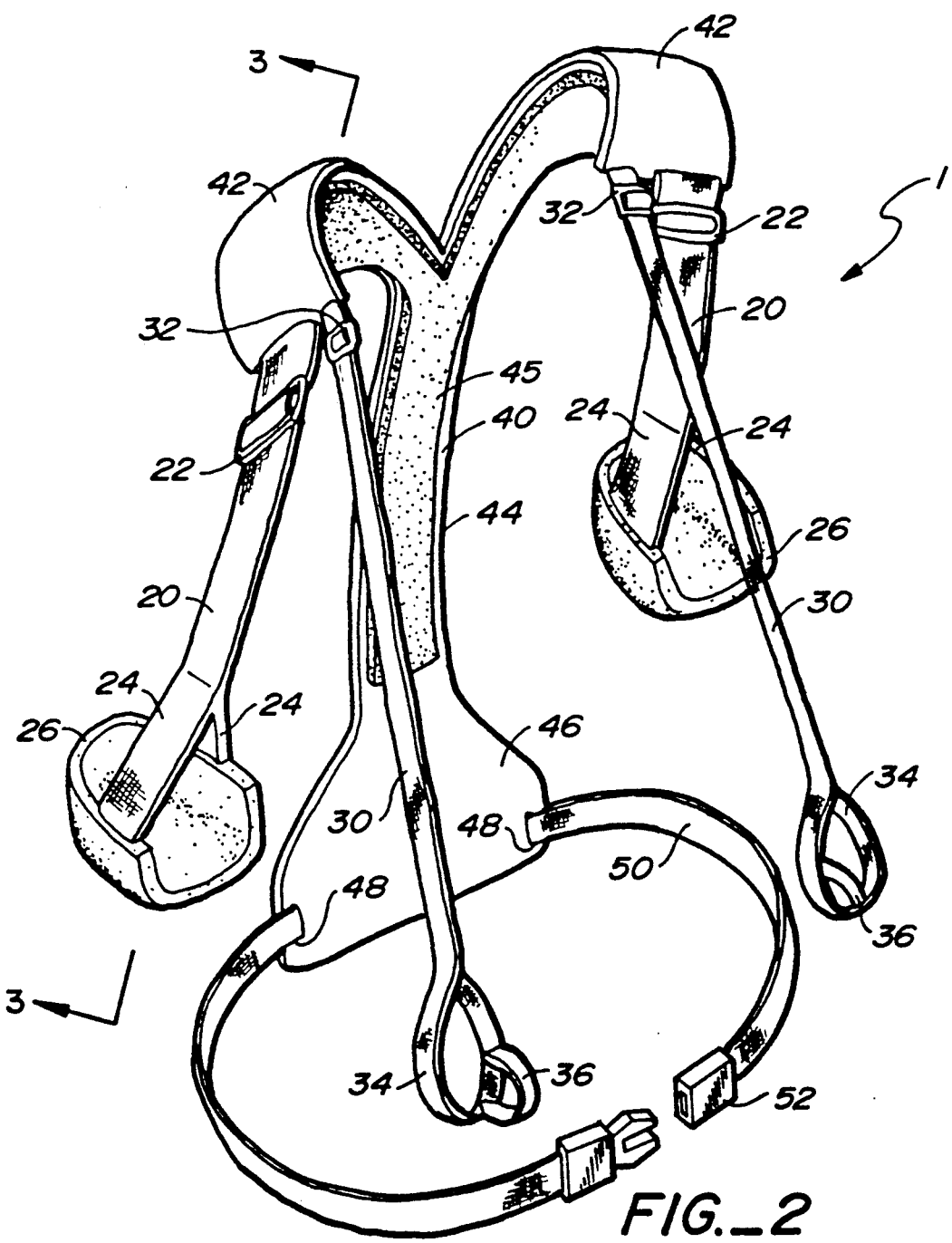
FIG._2

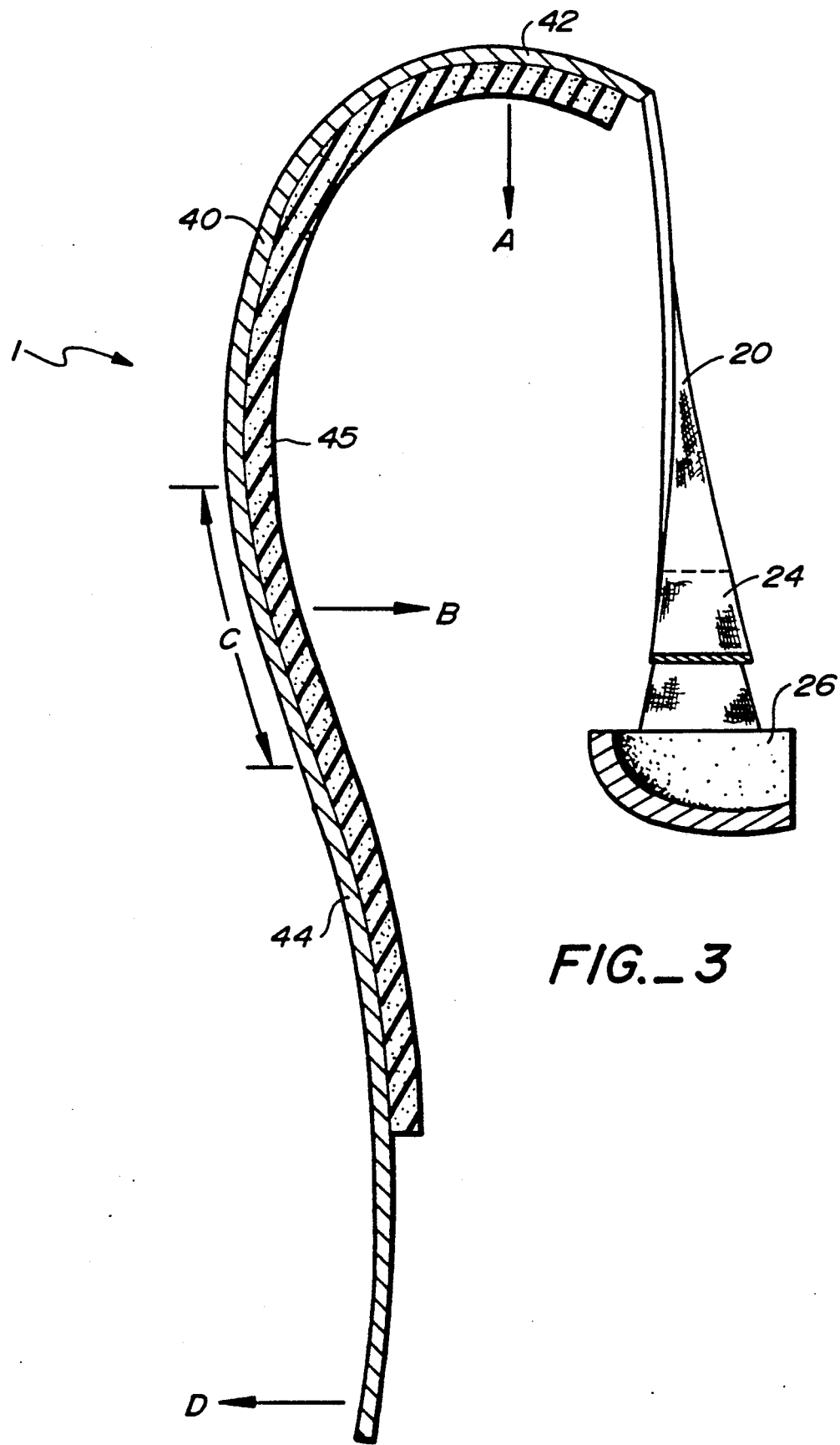
FIG._3

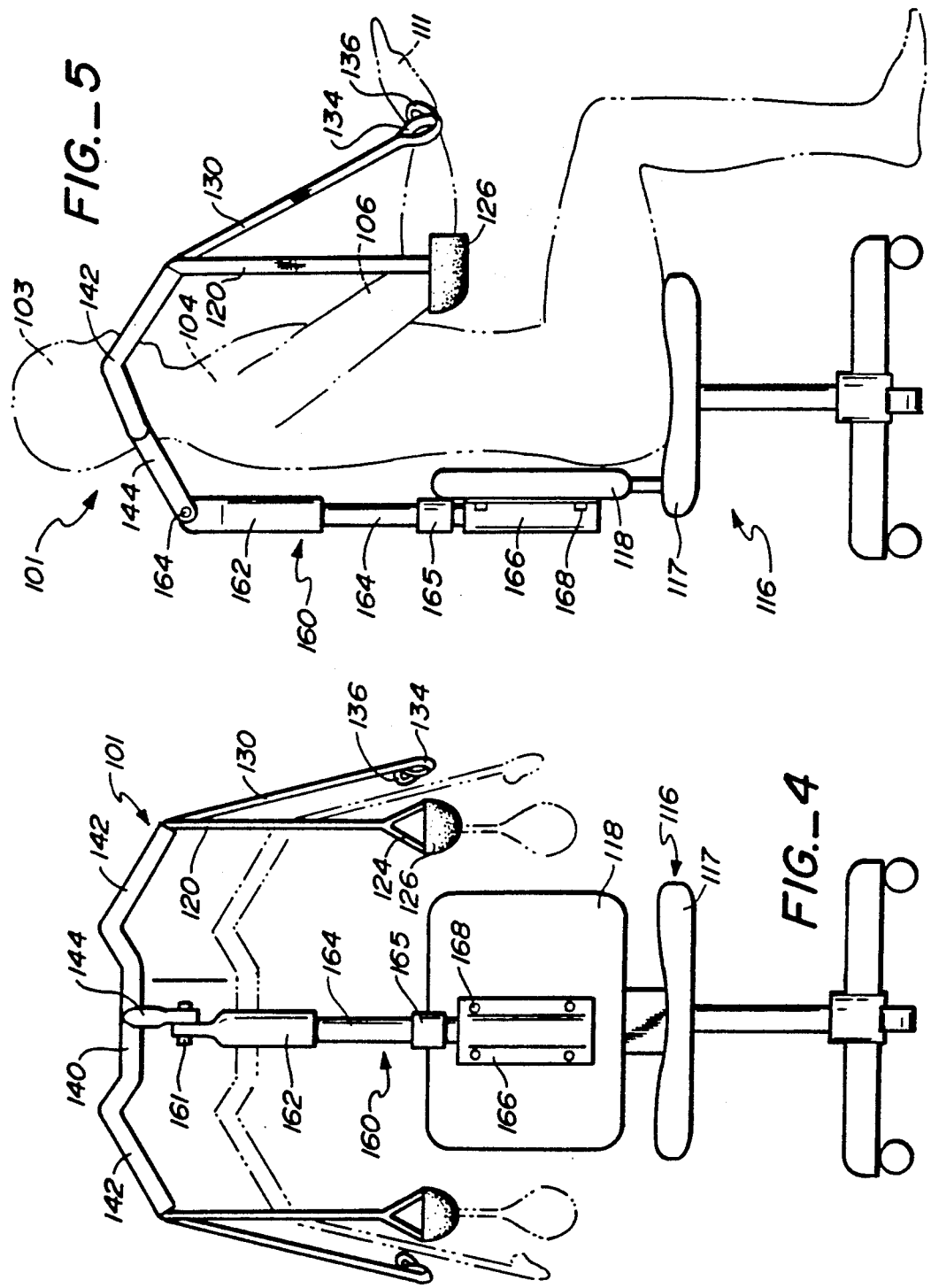

TYPING BRACE

FIELD OF THE INVENTION

This invention relates to arm support devices, more particularly to a rigid brace having elastic elbow and wrist straps for supporting a typist's hands while typing.

BACKGROUND OF THE INVENTION

With increased use of electric typewriters and computer keyboards has come a corresponding increase in the number of keyboard-related injuries, along with general complaints of pain and discomfort. Reports of back pain and wrist injuries, such as carpal tunnel syndrome, are believed to be related to the modern tendency of typists and computer operators to remain seated at a keyboard for long stretches of time without breaks or adjustments in posture. The leveraged weight placed by outstretched arms upon the typist's shoulders is a key area of concern. This can cause pain and injury to the neck and back. Similarly, constantly outstretching the fingers is one cause of wrist pain and injury. Even when injury does not result, the prolonged and continuous use of such keyboards can cause fatigue and other temporary discomfort.

Therefore, it is desired to describe herein a typing brace which relieves the neck, shoulders, back, elbows and wrists from the effects of improper loading, such as that which occurs when operating a typing keyboard.

Prior developments in this field may be generally illustrated by reference to the following patents:

| Patent No. | Patentee | Issue Date |
| --- | --- | --- |
| 9,828 | A. Day | Jul. 05, 1853 |
| 1,803,556 | J. Nugent | May 05, 1931 |
| 2,180,270 | F. Anderson, Jr. | Nov. 14, 1939 |
| 2,935,066 | V. Holloway | May 03, 1960 |
| 2,560,243 | M. Peterson | Jul. 10, 1951 |
| 4,302,849 | D. Margetson | Dec. 01, 1981 |
| 4,337,938 | B. Rodriguez | Jul. 06, 1982 |
| 4,751,923 | M. Marino | Jun. 21, 1988 |
| 4,815,639 | M. Lehman | Mar. 28, 1989 |
| 4,601,285 | P. Whitchurch | Jul. 22, 1986 |

U.S. Pat. No. 2,560,243 teaches a sling that provides support for both arms. It incorporates a garment that fits around the torso. It does not appear to disclose a rigid back yoke.

U.S. Pat. No. 4,302,849 teaches another soft garment having slings for both arms. Padding is incorporated beneath the shoulder straps.

U.S. Pat. No. 4,601,285 shows a vest with a single-arm sling that has two loops—one at the wrist and one back of the elbow. However, the elbow loop extends in back of the upper arm to provide lateral stability and does not wrap the forearm in any degree sufficient to provide vertical support. U.S. Pat. No. 2,935,066 also shows a single-arm sling with two loops. Both support the forearm.

U.S. Pat. No. 4,337,938 teaches a sling that is supported by the neck and supports both arms. It states that all of its straps can be made from elastic material. It also shows a hand grip that has separate loops for the fingers and for the thumb.

The rest of the patents are representative of what is in the art.

SUMMARY OF THE INVENTION

The present invention is a brace or sling which supports a typist's arms and wrists while seated at a keyboard. The two arms of a forked rigid yoke rest on the typist's shoulders. The body or leg of the yoke extends downward to the small of the typist's back, where it is anchored by a waist band. Two pairs of elastic straps extend down the front of the typist's chest, one pair from each arm of the yoke. One strap of each pair terminates in a cup for the typist's elbow. The other strap of the pair has a loop which cradles the typist's wrist. The second strap may have a small loop within the wrist loop into which fits the typist's thumb, in order to help keep the wrist loop in position.

The brace supports the typist's arms and wrists in the recommended typing position, relieving pressure due to gravity on the wrist and neck muscles. The levered pressure of the outstretched arms is distributed down the typist's back and waist. The elasticity of the straps allows the typist's hands and arms to retain a comfortable freedom of movement. The device thereby alleviates pain and discomfort in the wrist and neck and prevents many types of back, elbow or wrist injuries which are caused by prolonged periods at a keyboard.

FEATURES AND ADVANTAGES

An object of this invention is to disclose a typing brace apparatus which includes a rigid yoke having an upper pair of yoke arms, each yoke arm having a free forward end and a rear end connected to the rear end of the other yoke arm; a leg of the yoke depending downwardly from the connected rear ends of the yoke arms; and at least one strap depending downwardly from the forward end of each yoke arm, the strap having human arm cradling means at a distal end thereof. The brace further includes attachment means operably connected to the yoke leg for stabilizing the yoke leg with respect to the at least one strap.

A further object is to disclose an embodiment in which the attachment means is a waist band for encircling a human waist.

An alternate feature is two straps which depend downwardly from the forward end of each yoke arm, namely, a first strap of each pair comprising an elbow strap having an elbow cup at a distal end of the elbow strap, and a second strap of each pair comprising a wrist strap having a first human wrist engaging-loop at a distal end of the wrist strap.

Yet another feature is buckle means for adjusting the length of the straps.

Still another feature is, at the distal end of each wrist strap, a second human thumb engaging-loop attached to the first human wrist engaging-loop.

Another object is to disclose a triangular back plate depending downwardly from the yoke leg, to which back plate the waist band is affixed.

Still another feature is padding affixed to an inner surface of the yoke.

A further object is to disclose a second embodiment in which, instead of the waist band, the attachment means is a bracket for attaching the yoke leg to a chair.

A feature of the second embodiment is a telescoping rod which is connected between the bracket and the yoke leg for varying the effective height of the apparatus.

Another feature of the second embodiment is a pivot for rotatably attaching the telescoping rod means to the yoke leg.

Another object is to provide an apparatus which is easy to use, attractive in appearance and suitable for mass production at relatively low cost.

Other novel features which are characteristic of the invention, as to organization and method of operation, together with further objects and advantages thereof will be better understood from the following description considered in connection with the accompanying drawing in which a preferred embodiment of the invention is illustrated by way of example. It is to be expressly understood, however, that the drawing is for the purpose of illustration and description only and is not intended as a definition of the limits of the invention.

Certain terminology and derivations thereof may be used in the following description for convenience in reference only and will not be limiting. For example, the words "upwardly," "downwardly," "leftwardly," and "rightwardly" will refer to directions in the drawings to which reference is made. The words "inwardly" and "outwardly" will refer to directions toward and away from, respectively, the geometric center of a device and designated parts thereof.

BRIEF DESCRIPTION OF THE DRAWING

FIG. 1 is a perspective view of the typing brace of this invention, shown in use by a typist;

FIG. 2 is a perspective view of the device of FIG. 1, shown alone;

FIG. 3 is a schematic sectional view of the upper yoke portion of the device of FIGS. 1 and 2, taken generally along line 3—3 of FIG. 2;

FIG. 4 is a rear elevation of an alternate embodiment of the typing brace; and

FIG. 5 is a side elevation of the device of FIG. 4.

DRAWING REFERENCE NUMERALS

1: typing brace
3: typist
4: shoulder of 3
6: arm of 3
8: elbow of 3
9: forearm of 3
10: wrist of 3
11: hand of 3
13: thumb of 3
15: keyboard
16: chair
17: seat of 16
20: elbow strap of 1
22: buckle of 20
24: side band of 20
26: elbow cup of 20
30: wrist strap of 1
32: buckle of 30
34: wrist loop of 30
36: thumb loop of 30
40: yoke of 1
42: arm of 40
44: leg of 40
45: pad of 42,44
46: back plate of 40
48: aperture in 46
50: waist band
52: clasp of 50
101: typing brace
103: typist
104: shoulder of 103
106: arm of 103
111: hand of 103
116: chair
117: seat of 116
118: back of 116
120: elbow strap of 101
124: side band of 120
126: elbow cup of 120
130: wrist strap of 101
134: wrist loop of 130
136: thumb loop of 130
140: yoke of 101
142: arm of 140
144: leg of 140
160: support assembly for 140
161: pivot between 144,162
162: cap of 160
164: rod of 160
165: sleeve clamp for 164
166: bracket of 160
168: screw for 166

DESCRIPTION OF A PREFERRED EMBODIMENT

Referring to FIGS. 1 and 2, there is illustrated therein a typing brace 1 of this invention. The brace is used in the following environment. A typist 3 has the normal human anatomy, namely, shoulders 4, arms 6, elbows 8, forearms 9, wrists 10, hands 11, and thumbs 13. The typist 3 is shown operating the keyboard 15 of a computer or a typewriter, while seated on a chair 16 having a seat 17.

The brace 1 is generally comprised of the following parts: a pair of adjustable elastic-cloth elbow straps 20; a pair of adjustable elastic wrist straps 30; a rigid yoke 40 made of plastic or metal, from which the two pairs of straps downwardly depend; and a waist band 50 attached to the bottom of the yoke. While relatively thin plates of either metal or molded plastic as used herein will flex somewhat, they may be considered "rigid" for present purposes, especially when compared to the elasticity and flexibility of cloth.

Much of the benefit from using the device flows from the support given by the elbow straps 20 to the typist's elbows 8 and to the proximal portion of the forearm 9. Additional benefit, particularly toward eliminating pain and fatigue in the typist's wrists 10, comes from supporting those wrists with the wrist straps 30. However, the wrist straps may be considered ungainly or inconvenient in some applications, particularly those wherein the device must be applied and removed repeatedly or wherein the typist works at a public location where appearances perhaps may be considered to be important. Therefore, the wrist straps 30 could be optional, although they ar included in the preferred embodiment.

The yoke 40 is generally "Y" shaped. Thus, it can be described as being comprised of a pair of upwardly and forwardly extending arms 42 which diverge from their intersection with a downwardly depending leg or body 44. The inwardly facing (with respect to the body of the typist 3) surfaces of the arms 42 and leg 44 of the yoke are lined with appropriate padding 45. While the padding 45 is shown comprising one piece in the drawing, it could be divided into separate pads, one for each arm of the yoke and one for its leg. Means for allowing the padding 45 to be shifted according to the fit and comfort of the typist, such as VELCRO brand hook and loop fastening material (not illustrated), could be included.

The leg 44 of the yoke 40 descends to a generally triangular back plate 46. An adjustable waist band 50 passes through apertures 48 in the back plate 46, or is otherwise affixed to the back plate. The waist band is fastened by a clasp 52 so as to comfortably encircle the waist of typist 3 when the device is worn. The waist band 50 keeps the back plate 46 against the lower section of the back of the typist and prevents the back plate from being levered out away from the back during use. The band stabilizes the yoke leg 44 with respect to the straps 20,30 in that; while the straps are free to swing in relation to the trunk of the typist's body, the yoke leg is not.

Each elastic elbow strap 20 is affixed at its upper end to the forward end of an associated yoke arm 42. Its overall length may be adjusted with a buckle 22. At its lower end, each elbow strap 20 bifurcates into a pair of side bands 24 that are used to support the sides of an elbow cup 26, thereby cradling the typist's arm 6. Alternatively, the side bands could continue upward until meeting at the buckle 22, an arrangement into which it may be somewhat easier for the typist to insert his or her arms. The cup 26 forms an internal cavity whose shape approximately matches the external contour of the human elbow area. This shape supports the typist's elbow 8 both at the rear and forwardly at the immediately proximal portion of the typist's forearm 9. The elbow cups 26 may be made of cloth and may incorporate foam padding and/or rigid internal shaping members (not illustrated).

Each optional elastic wrist strap 30 is affixed at its upper end to the forward end of an associated yoke arm 42, next to the point of attachment of the elbow strap 20, which is associated with the same arm 6 of the typist. The length of the wrist straps may be adjusted with buckles 32. At its lower end, each wrist strap forms a wrist loop 34 which supports the typist's wrist 10 and hand 11, thereby cradling the typist's arm 6 at a second point. A smaller thumb loop 36 may be sewn into the inner surface of the wrist loop 34. When the typist's thumb 13 is engaged in the thumb loop 36, the wrist loop 34 is prevented from sliding backward along the typist's forearm 9.

Turning to the schematic illustration of FIG. 3, it can be seen how a significant portion of the weight of the typist's outstretched arms 6 is distributed away from his or her shoulders 4 through use of the brace 1 of the present invention. Each elbow strap 20 (and wrist strap 30—not shown in FIG. 3) pulls down on the end of its individual yoke arm 42. While some of the pressure is exerted against the typist's shoulders 4 in the direction of arrow A, some of it is distributed down the length of his or her spine in the direction of arrow B. The entire rigid yoke 40 acts as a lever in distributing this force. Area C in the small of the typist's back (i.e. the thoracic curve in the vicinity of vertebrae T5-T9) acts as the fulcrum of this lever, so that the force in the area of the lower back plate 46 actually pulls away from the typist's body in the direction of arrow D. However, the waist band 50 allows the typist's waist to counteract this tendency and to keep the yoke 40 snug and stable against the typist's back.

FIGS. 4 and 5 illustrate a second embodiment of the invention, namely, typing brace 101. It is to be noted that, for convenience, the last two positions of the reference numerals of the alternate embodiment of the invention duplicate those of the numerals of the embodiment of FIG. 1, where reference is made to similar or corresponding parts.

The brace 101 is generally comprised of the following parts: a pair of adjustable elastic elbow straps 120; a pair of adjustable elastic wrist straps 130; a rigid yoke 140 made of plastic or metal (preferably tubular in construction), from which the two pairs of straps downwardly depend; and a chair support assembly 160 attached to the bottom of the yoke. As in the previous embodiment, the wrist straps 130 may or may not be considered optional, depending on the use to which the brace 101 is to be put.

The yoke 140 is generally "Y" shaped. It is comprised of a pair of upwardly and forwardly extending arms 142 which diverge from their intersection with a downwardly depending leg 144. The leg of the yoke 140 terminates in an adjustable pivot 161.

The pivot 161 attaches the leg of the yoke to an assembly 160 for supporting the typing brace from the back 118 of a chair 116. The support assembly stabilizes the leg 144 and arms 142 of the yoke with respect to the free-swinging straps 120,130. A tubular sleeve or cap 162 connects the adjustable pivot 161 to a sliding rod 164. A sleeve clamp 165 of known and standard design allows the rod 164 to be adjustably telescoped up and down within a tube affixed within a bracket 166. The bracket 166 may be affixed to the back 118 of a chair 116 by any of a number of equivalent means, preferably with screws 168. Alternatively, the bracket could be formed to bend horizontal, i.e. parallel to the floor (not illustrated). Appropriately cushioned, it then could rest on top of the seat 117 of the chair and be held in place simply by the weight of the typist's body.

Each elastic elbow strap 120 is affixed at its upper end to the forward end of an associated yoke arm 142. Its overall length is suitably adjustable. At its lower end, each elbow strap bifurcates into a pair of side bands 124 that are used to support the sides of a shaped elbow-cup 126.

Each elastic wrist strap 130 is affixed at its upper end to the forward end of an associated yoke arm 142, next to the point of attachment of the elbow strap 120 which is associated with the same arm of the typist 103. The wrist straps include means for making their length suitably adjustable. At its lower end, each wrist strap forms a wrist loop 134 which supports the typist's wrist and hand. A smaller thumb loop 136 may be sewn onto the wrist loop 134.

As can be seen in FIG. 5, the chair-supported typing brace 101 preferably will be adjusted (by means of the sleeve clamp 165 and the pivot 161) so as not to rest on the typist's shoulders 104 at all. Therefore, nearly all of the weight of the typist's arms 106 and hands 111 is taken off of his or her shoulders and back and is transferred to the chair 116.

Since neither the typist's pelvis nor the back of the chair move during typing, the waist band 50 and bracket 166 may be viewed as alternate means for keeping stable the legs 44,144 of the two embodiments 1,101, especially with respect to the freely moving straps 20,30,120,130.

The elasticity of the straps 20,30,120,130 allows the hands to retain a remarkable freedom of movement, while the support the straps give to the arms causes the fingers to feel as if they are effortlessly floating above the keyboard. Both embodiments 1,101 of this invention result in an exceptional improvement in typing comfort and safety, thereby reducing injury and stress on the job.

While the above provides a full and complete disclosure of the preferred embodiments of this invention, various modifications, alternate constructions, and equivalents may be employed without departing from the true spirit and scope of the invention. Such changes might involve alternate materials, components, structural arrangements, sizes, operational features or the like. Therefore, the above description and illustrations should not be construed as limiting the scope of the invention which is defined by the appended claims.

What is claimed is:

1. Typing brace apparatus including:
   a rigid yoke having an upper pair of yoke arms, each yoke arm having a free forward end and a rear end connected to the rear end of the other yoke arm;
   a leg of the yoke depending downwardly from the connected rear ends of the yoke arms;
   at least one strap depending downwardly from the forward end of each yoke arm, the at least one strap having human arm cradling means at a distal end thereof; and
   attachment means operably connected to the yoke leg for stabilizing the yoke leg with respect to the at least one strap.

2. The apparatus of claim 1 wherein:
   the attachment means is a waist band for encircling a human waist.

3. The apparatus of claim 2 further including:
   padding on at least the interconnected rear ends of the yoke arms.

4. The apparatus of claim 1 wherein:
   the attachment means is a bracket for attaching the yoke leg to a chair.

5. Typing brace apparatus including:
   a rigid yoke having an upper pair of yoke arms, each yoke arm having a free forward end and a rear end connected to the rear end of the other yoke arm;
   a leg of the yoke depending downwardly from the connected rear ends of the yoke arms;
   a waist band for encircling a human waist operably connected to the yoke leg; and
   two straps depending downwardly from the forward end of each yoke arm, namely,
      a first strap of each of the yoke arms comprising an elbow strap having an elbow cup at a distal end of the elbow strap, and
      a second strap of each of the yoke arms comprising a wrist strap having a first human wrist engaging-loop at a distal end of the wrist strap.

6. The apparatus of claim 5 further including:
   means for adjusting the length of the straps.

7. The apparatus of claim 6 further including:
   at the distal end of each wrist strap, a second human thumb engaging-loop attached to the first human wrist engaging-loop.

8. The apparatus of claim 7 further including:
   a triangular back plate depending downwardly from the yoke leg, to which back plate the waist band is affixed.

9. The apparatus of claim 8 further including:
   padding affixed to an inner surface of the yoke.

10. Typing brace apparatus including:
    a rigid yoke having an upper pair of yoke arms, each yoke arm having a free forward end and a rear end connected to the rear end of the other yoke arm;
    a leg of the yoke depending downwardly from the connected rear ends of the yoke arms;
    at least one strap depending downwardly from the forward end of each yoke arm, the at least one strap having human arm cradling means at a distal end thereof;
    a bracket operably connected to the yoke leg for attaching the yoke leg to a chair; and
    telescoping rod means connected between the bracket and the yoke leg for varying the effective height of the apparatus.

11. The apparatus of claim 10 further including:
    a pivot for rotatably attaching the telescoping rod means to the yoke leg.

12. The apparatus of claim 11 wherein:
    there are two straps depending downwardly from the forward end of each yoke arm, namely,
       a first strap of each pair comprising an elbow strap having an elbow cup at a distal end of the elbow strap, and
       a second strap of each pair comprising a wrist strap having a first human wrist engaging-loop at a distal end of the wrist strap.

13. The apparatus of claim 12 further including:
    means for adjusting the length of the straps.

14. The apparatus of claim 13 further including:
    at the distal end of each wrist strap, a second human thumb engaging-loop attached to the first human wrist engaging-loop.

15. Typing brace apparatus including:
    a rigid yoke having an upper pair of yoke arms, each yoke arm having a free forward end and a rear end connected to the rear end of the other yoke arm;
    a leg of the yoke depending downwardly from the connected rear ends of the yoke arms;
    padding affixed to an inner surface of the yoke;
    a pair of straps depending downwardly from the forward end of each yoke arm, namely,
       a first strap of each pair comprising an elbow strap having an elbow cup at a distal end of the elbow strap, and
       a second strap of each pair comprising a wrist strap having a first human wrist engaging-loop at a distal end of the wrist strap;
    means for adjusting the length of the straps; and
    a waist band for encircling a human waist, the waist band operably connected to the yoke leg for stabilizing the yoke leg with respect to the human waist and to the two pairs of straps.

16. The apparatus of claim 15 further including:
    at the distal end of each wrist strap, a second human thumb engaging-loop attached to an inner surface of the first human wrist engaging-loop.

17. Typing brace apparatus including:
    a rigid yoke having an upper pair of yoke arms, each yoke arm having a free forward end and a rear end connected to the rear end of the other yoke arm;
    a leg of the yoke depending downwardly from the connected rear ends of the yoke arms;
    two straps depending downwardly from the forward end of each yoke arm, namely,
       a first strap of each pair comprising an elbow strap having an elbow cup at a distal end of the elbow strap, and
       a second strap of each pair comprising a wrist strap having a first human wrist engaging-loop at a distal end of the wrist strap;
    means for adjusting the length of the straps;

a bracket for attaching the yoke leg to a chair, the bracket operably connected to the yoke leg, for stabilizing the yoke leg with respect to the two pairs of straps;

telescoping rod means connected between the bracket and the yoke leg for varying the effective height of the apparatus; and a pivot for rotatably attaching the telescoping rod means to the yoke leg.

18. The apparatus of claim 17 further including:

at the distal end of each wrist strap, a second human thumb engaging-loop attached to an inner surface of the first human wrist engaging-loop.

19. Typing brace apparatus including:

a rigid yoke having at least one upper yoke arm, the at least one yoke arm having a free forward end and a rear end;

a leg of the yoke connected to and depending downwardly from the rear end of the at least one yoke arm;

at least one strap depending downwardly from the forward end of the at least one yoke arm, the at least one strap having human arm cradling means at a distal end thereof; and attachment means operably connected to the yoke leg for stabilizing the yoke leg with respect to the at least one strap.

* * * * *